(12) United States Patent (10) Patent No.: US 11,130,041 B2
Kim (45) Date of Patent: Sep. 28, 2021

(54) SYSTEM FOR PROVIDING A VIRTUAL EXERCISE PLACE

(71) Applicant: Jae Hwan Kim, Jeollanam-do (KR)

(72) Inventor: Jae Hwan Kim, Jeollanam-do (KR)

( * ) Notice: Subject to any disclaimer, the term of this patent is extended or adjusted under 35 U.S.C. 154(b) by 206 days.

(21) Appl. No.: 16/572,209

(22) Filed: Sep. 16, 2019

(65) Prior Publication Data

US 2020/0009425 A1 Jan. 9, 2020

Related U.S. Application Data

(63) Continuation-in-part of application No. 16/101,712, filed on Aug. 13, 2018, now Pat. No. 10,449,435.

(30) Foreign Application Priority Data

Nov. 15, 2017 (KR) .......................... 10-2017-0152555

(51) Int. Cl.
*A63B 71/06* (2006.01)
*G16H 20/30* (2018.01)
(Continued)

(52) U.S. Cl.
CPC ...... *A63B 71/0622* (2013.01); *A63B 24/0059* (2013.01); *A63B 24/0087* (2013.01);
(Continued)

(58) Field of Classification Search
CPC ............ A63B 71/0619; A63B 71/0622; A63B 2024/0081; A63B 2071/0625;
(Continued)

(56) References Cited

U.S. PATENT DOCUMENTS

| 13,712 | A | * | 10/1855 | Yard | .......................... | B62C 5/04 |
| | | | | | | 278/113 |
| 43,325 | A | * | 6/1864 | Merrill | .................... | C10G 19/00 |
| | | | | | | 208/284 |

(Continued)

FOREIGN PATENT DOCUMENTS

KR 1020050021032 A 3/2005
KR 10-2007-0043325 A 10/2007
(Continued)

OTHER PUBLICATIONS

Korean Patent Application No. 10-2017-0152555, Grant of Patent dated Mar. 27, 2018, 2 pages.
(Continued)

*Primary Examiner* — Garrett K Atkinson
(74) *Attorney, Agent, or Firm* — Avant Law Group, LLC

(57) ABSTRACT

A virtual exercise place selected by a user is displayed and the user can exercise while sharing the display of the selected virtual exercise place with another user in real time or at a different time. The system has an image information database in which location-based image data related to a virtual exercise place is stored; and an image data controller selecting from the image information database location-based image data related to a virtual exercise place received from the terminal and providing the selected location-based image data to the terminal, displaying on the terminal an exercise place image data corresponding to an exercise start location received from the terminal, receiving exercise distance information calculated by the fitness equipment, and displaying on the terminal an exercise place image data corresponding to a location moved by the exercise distance from the exercise start location.

6 Claims, 10 Drawing Sheets

(51) Int. Cl.
| | |
|---|---|
| *A63B 24/00* | (2006.01) |
| *G06F 16/538* | (2019.01) |
| *G06F 3/0482* | (2013.01) |
| *G06F 3/14* | (2006.01) |
| *G06F 3/147* | (2006.01) |
| *G06Q 30/02* | (2012.01) |
| *H04N 7/14* | (2006.01) |
| *G09G 5/36* | (2006.01) |
| *A63B 22/02* | (2006.01) |
| *A63B 22/06* | (2006.01) |
| *H04L 29/06* | (2006.01) |

(52) U.S. Cl.
CPC ........ *A63B 71/0619* (2013.01); *G06F 3/0482* (2013.01); *G06F 3/147* (2013.01); *G06F 3/1454* (2013.01); *G06F 16/538* (2019.01); *G06Q 30/0277* (2013.01); *G09G 5/36* (2013.01); *G16H 20/30* (2018.01); *H04N 7/141* (2013.01); *H04N 7/147* (2013.01); *A63B 22/02* (2013.01); *A63B 22/025* (2015.10); *A63B 22/06* (2013.01); *A63B 22/0605* (2013.01); *A63B 24/0084* (2013.01); *A63B 2024/009* (2013.01); *A63B 2024/0081* (2013.01); *A63B 2024/0093* (2013.01); *A63B 2024/0096* (2013.01); *A63B 2071/0625* (2013.01); *A63B 2071/0636* (2013.01); *A63B 2071/0644* (2013.01); *A63B 2071/0675* (2013.01); *A63B 2220/12* (2013.01); *A63B 2220/18* (2013.01); *A63B 2220/20* (2013.01); *A63B 2220/806* (2013.01); *A63B 2220/807* (2013.01); *A63B 2220/808* (2013.01); *A63B 2225/20* (2013.01); *A63B 2225/50* (2013.01); *G09G 2354/00* (2013.01); *H04L 67/42* (2013.01)

(58) Field of Classification Search
CPC .... A63B 2071/0636; A63B 2071/0638; A63B 2071/0644; A63B 2220/808; A63B 2220/18; A63B 2024/0096; A63B 2220/807; A63B 2024/0093; A63B 22/025; A63B 2220/20; A63B 2071/0675; A63B 2225/50; A63B 22/0605; A63B 2225/20; A63B 2220/806; A63B 2024/009; A63B 24/0084; A63B 2024/0025; A63B 2220/05; A63B 2220/14; A63B 2220/833; A63B 24/0062; A63B 2225/09; A63B 24/0087; A63B 24/0059; A63B 22/02; A63B 22/06; A63B 2220/12; A63B 2024/0065; A63B 2024/0068; A63B 2024/0071; A63B 2024/0078; A63B 2071/0627; A63B 2071/0633; A63B 2071/0641; A63B 24/00; A63B 24/0075; A63B 71/00; A63B 71/06; G06F 19/30; G06F 19/32; G06F 19/321; G06F 19/324; G06F 19/325; G06F 19/328; G06F 19/34; G06F 19/3418; G06F 19/3481; G06F 3/14; G06F 16/538; G06F 3/0482; G06F 3/1454; G06F 3/147; G06Q 50/22; G06Q 50/24; G06Q 30/0277; G16H 20/00; G16H 20/30; H04N 7/147; H04N 7/141; G09G 2354/00; G09G 5/36; H04L 67/42
See application file for complete search history.

(56) References Cited

U.S. PATENT DOCUMENTS

| | | | | |
|---|---|---|---|---|
| 88,184 | A * | 3/1869 | Lafferty et al. | B04B 11/08 210/368 |
| 117,104 | A * | 7/1871 | Northup | E04F 19/062 52/468 |
| 152,555 | A * | 6/1874 | Gorton | A63H 33/40 446/245 |
| 1,675,331 | A * | 7/1928 | Day | B42F 17/00 40/398 |
| 1,780,743 | A * | 11/1930 | Codwise | D21J 1/16 162/103 |
| 1,803,507 | A * | 5/1931 | O'Neill | B64F 1/36 244/110 E |
| 1,831,730 | A * | 11/1931 | Ahlberg | H04Q 1/36 379/341 |
| 3,103,517 | A * | 9/1963 | Prosser | C07D 307/73 548/195 |
| 6,152,856 | A * | 11/2000 | Studor | G16H 20/30 482/8 |
| 7,497,812 | B2 * | 3/2009 | Neff | A63B 21/008 482/51 |
| 7,833,135 | B2 * | 11/2010 | Radow | A63B 71/0622 482/57 |
| 8,021,270 | B2 * | 9/2011 | D'Eredita | A63B 24/0087 482/8 |
| 8,103,517 | B2 * | 1/2012 | Hinnebusch | A63B 24/0084 705/1.1 |
| 10,610,725 | B2 * | 4/2020 | Schaefer | A63B 24/0075 |
| 2002/0055419 | A1 * | 5/2002 | Hinnebusch | G16H 40/67 482/8 |
| 2004/0088184 | A1 * | 5/2004 | Nijdam | G06Q 30/016 706/45 |
| 2007/0043325 | A1 * | 2/2007 | Guala | A61M 5/1411 604/252 |
| 2007/0093360 | A1 * | 4/2007 | Neff | G06F 3/03 482/8 |
| 2009/0011907 | A1 * | 1/2009 | Radow | A63B 24/0084 482/57 |
| 2009/0023553 | A1 * | 1/2009 | Shim | A63B 71/0622 482/4 |
| 2009/0023554 | A1 * | 1/2009 | Shim | A63F 13/245 482/4 |
| 2010/0004097 | A1 * | 1/2010 | D'Eredita | G16H 50/20 482/8 |
| 2012/0117104 | A1 * | 5/2012 | Stundner | G06Q 10/00 707/769 |
| 2014/0046677 | A1 * | 2/2014 | Bar-Or | G16H 20/60 705/2 |
| 2015/0302766 | A1 * | 10/2015 | Oberlander | G06Q 10/10 434/247 |
| 2017/0152555 | A1 * | 6/2017 | Inoue | C12N 15/09 |
| 2018/0013712 | A1 * | 1/2018 | Yin | H04L 67/125 |
| 2018/0099178 | A1 * | 4/2018 | Schaefer | A63B 24/0084 |

FOREIGN PATENT DOCUMENTS

| | | |
|---|---|---|
| KR | 1020070115210 A | 12/2007 |
| KR | 100853993 B1 | 8/2008 |
| KR | 1020090129077 A | 12/2009 |
| KR | 1020100113945 A | 10/2010 |
| KR | 10-2012-0117104 A | 10/2012 |
| KR | 101461202 B1 | 11/2014 |
| KR | 10-1780743 B1 | 9/2017 |
| KR | 10-2017-0009376 B1 | 11/2017 |
| KR | 10-1803507 B1 | 11/2017 |
| KR | 10-1831730 B1 | 2/2018 |
| KR | 101874262 B1 | 7/2018 |
| WO | 2016132844 A1 | 8/2016 |

OTHER PUBLICATIONS

Korean Patent Application No. 10-2017-0152555, Office Action dated Dec. 12, 2017, 12 pages.

(56) References Cited

OTHER PUBLICATIONS

Korean Patent Application No. 10-2017-0152555, Certificate of Patent, 1 page.

* cited by examiner

SYSTEM FOR PROVIDING A VIRTUAL EXERCISE PLACE

CROSS-REFERENCE TO RELATED APPLICATION

This application is a continuation-in-part of U.S. patent application Ser. No. 16/101,712 filed Aug. 13, 2018, which claims priority to and the benefit of Korean Patent Application No. 10-2017-0152555 filed on Nov. 15, 2017. The above applications are all hereby incorporated by reference for all purposes as if fully set forth herein.

TECHNICAL FIELD

Some implementations of the disclosed technology relate to a system for providing a virtual exercise place, wherein the virtual exercise place selected by a user is displayed and the user can take exercise while sharing the display of the selected virtual exercise place with another user in real time or at a time difference.

BACKGROUND

The importance of exercise cannot be emphasized enough. However, the problem is that exercise cannot continue for a long period because it is boring and difficult. In particular, exercise alone, for example, walking, running or cycling is exercise that a user alone has to achieve a target amount without a partner. A user requires a strong will in order to continue exercise for a long period. In general, in the case of exercise alone, a user brightens up dull moments while watching a movie or broadcast program from a monitor positioned on the front of fitness equipment. However, it is difficult to find out a movie or broadcast program suitable for an exercise time every time. As a result, this makes it difficult to maintain an interest in exercise for a long period.

Exercise alone may continue for a long period when it is taken along with a partner. To this end, a user may use treadmills or cycling equipment positioned in parallel along with a partner. In this case, the number of partners with whom a user can talk and exercise are not more than two persons left and right. In particular, partners must arrive at an exercise place on an agreed time and place and pieces of not-occupied fitness equipment positioned in parallel must be secured. As a result, not losing an interest in exercise for a long period is limited.

SUMMARY

Various implementations are provided to introduce a unique manner of providing a virtual exercise place, wherein a virtual exercise place selected by a user is displayed on a screen around fitness equipment and the user can take exercise along with another user while sharing the display of the selected virtual exercise place with another user in real time or at a time difference so that the user can take exercise while virtually moving within the selected virtual exercise place.

Some implementations of the disclosed technology provide a system for providing a virtual exercise place, which is connected to a terminal and fitness equipment capable of calculating an exercise distance and transmits an image of a virtual exercise place to the terminal. In some implementations, the system comprises: an image information database in which location-based image data related to a virtual exercise place is stored; and an image data controller selecting from the image information database location-based image data related to a virtual exercise place received from the terminal and providing the selected location-based image data to the terminal, displaying in the terminal an image corresponding to an exercise start location received from the terminal, receiving exercise distance information calculated by the fitness equipment, and displaying in the terminal an image corresponding to a location moved by the exercise distance from the exercise start location (hereinafter referred to as a "virtual current location").

In one aspect, when the virtual current location reaches a course selection point of the location-based image data, the image data controller transmits a course selection message to the terminal and displays in the terminal an image corresponding to a course selected from the terminal.

In another aspect, the image information database comprises gradient data of each location of the location-based image data, and the system further comprises a slope activation unit connected to a load control device of the fitness equipment and applying to the fitness equipment a load based on gradient data corresponding to the virtual current location.

Some implementations of the disclosed technology provide a system for providing a virtual exercise place, which is connected to terminals and fitness equipment capable of calculating exercise distances and transmits an image of a virtual exercise place to the terminals. In some implementations, the system comprises: an image information database in which location-based image data related to a virtual exercise place is stored; a participant setting unit transmitting to a second terminal a signal asking an exercise participation intention received from a first terminal and receiving an exercise participation approval signal from the second terminal; and an image data controller selecting from the image information database location-based image data related to a virtual exercise place received from the first terminal and transmitting the selected location-based image data to the first terminal and the second terminal, displaying in the first terminal and the second terminal an image corresponding to an exercise start location received from the first terminal or the second terminal, receiving exercise distance information calculated by first fitness equipment and second fitness equipment, and displaying in the first terminal and the second terminal an image corresponding to a location moved by the exercise distance from the exercise start location (hereinafter referred to as a "virtual current location").

In one aspect, when the virtual current location reaches a course selection point of the location-based image data, the image data controller transmits a course selection message to the first terminal and the second terminal and displays in the first terminal and the second terminal an image corresponding to a course first selected by any one of the first terminal and the second terminal.

In another aspect, each of the first terminal and the second terminal comprises a camera and a microphone, and the system further comprises a video chatting controller receiving from the first terminal and the second terminal video data of a first user using the first terminal and a second user using the second terminal, photographed by the cameras of the first terminal and the second terminal, and audio data comprising voices of the first user and the second user, recorded by the microphones of the first terminal and the second terminal, transmitting the video data and audio data of the first user to the second terminal, and transmitting the video data and audio data of the second user to the first terminal.

In another aspect, the image information database comprises gradient data of each location of the location-based image data, and the system further comprises a slope activation unit connected to load control devices of the first fitness equipment and the second fitness equipment and applying to the first fitness equipment and the second fitness equipment a load based on gradient data corresponding to the virtual current location.

According to the implementations of the disclosed technology, a mechanism is provided to display a virtual exercise place selected by a user on a screen around fitness equipment, enable a user to take exercise while virtually moving within the selected virtual exercise place, and enable the user to take exercise while sharing the display of the selected virtual exercise place with another user whom the user meets in the virtual exercise space.

Some implementations of the disclosed technology provide a system for providing a virtual exercise place, which is connected to terminals comprising a camera and a microphone and fitness equipment capable of calculating exercise distances and transmits an image of a virtual exercise place to the terminals. In some implementations, the system comprises: an image information database in which location-based image data related to a virtual exercise place is stored; a participant setting unit transmitting to a second terminal a signal asking an exercise participation intention received from a first terminal and receiving an exercise participation approval signal from the second terminal; an image data controller selecting from the image information database location-based image data related to a virtual exercise place received from the first terminal and transmitting the selected location-based image data to the first terminal and the second terminal, displaying in the first terminal and the second terminal an image corresponding to an exercise start location received from the first terminal or the second terminal, receiving exercise distance information calculated by first fitness equipment and second fitness equipment, and displaying in the first terminal and the second terminal an image corresponding to a location moved by the exercise distance from the exercise start location (hereinafter referred to as a "virtual current location"); and a video chatting controller receiving from the first terminal and the second terminal video data of a first user using the first terminal and a second user using the second terminal, photographed by the cameras of the first terminal and the second terminal, and audio data comprising voices of the first user and the second user, recorded by the microphones of the first terminal and the second terminal, transmitting the video data and audio data of the first user to the second terminal, and transmitting the video data and audio data of the second user to the first terminal, wherein when a virtual current location of a third terminal to which the first terminal did not transmit a signal asking an exercise participation intention is close to the virtual current location of the first terminal or the second terminal, the video chatting controller receives from the third terminal video data of a third user using the third terminal, photographed by the camera of the third terminal, and audio data comprising voices of the third user, recorded by the microphone of the third terminal, transmits the video data and audio data of the third user to the first terminal and the second terminal, and transmits the video data and audio data of the first user and the second user to the third terminal, and wherein when the third terminal transmits a joint signal to the first terminal or the second terminal through the participant setting unit, the video chatting controller displays in the third terminal an image corresponding to the virtual current location of the first terminal and the second terminal.

Some implementations of the disclosed technology provide a system for providing a virtual exercise place, which is connected to terminals and fitness equipment capable of calculating an exercise distance and transmits an image of an virtual exercise place to the terminals, the system comprising: an image information database in which location-based image data related to a virtual exercise place is stored; an image data controller selecting from the image information database location-based image data related to a virtual exercise place (hereinafter referred to as "exercise place image data") received from the first terminal and transmitting the selected exercise place image data to the first terminal, displaying on the first terminal the exercise place image data corresponding to an exercise start location received from the first terminal, receiving exercise distance information calculated by first fitness equipment, and displaying on the first terminal the exercise place image data corresponding to a location moved by the exercise distance from the exercise start location (hereinafter referred to as "current location"); and an exercise record database storing exercise place image data from the exercise start location to the current location (hereinafter referred to as "first exercise place image data"), displayed on the first terminal, wherein when the image data controller receives the joint exercise start signal input from the second terminal, the image data controller may display the first exercise place image data on the second terminal.

The image data control unit receives the movement distance information calculated by the second fitness equipment and displays the first exercise place image data on the second terminal so that the current location of the second fitness equipment coincides with the current location of the first exercise place image data.

The system further includes a fitness equipment controller controlling the speed of the second fitness equipment, wherein the fitness equipment controller can change the speed of the second fitness equipment in accordance with the speed at which the current location of the first exercise place image data changes.

The first terminal includes a camera and a microphone, and the first exercise place image data may include the video data of the first user using the first fitness equipment, photographed by the camera of the first terminal, and the audio data including the voice of the first user, recorded by the microphone of the first terminal.

The second terminal includes a camera and a microphone, and the system further comprises an exercise result transmitting unit which displays the video data of the second user using the second fitness equipment, photographed by the camera of the second terminal and transmit the image data displayed on the second terminal to the member account of the first user.

The second terminal and the third terminal include a camera and a microphone, and the system further comprises a video chat controller which receives from the second terminal and the third terminal the video data of the second user using the second terminal and the third user using the third terminal, photographed by the cameras of the second terminal and the third terminal, and the audio data including the voice of the second user and the third user, recorded by the microphones of the second terminal and the third terminal, transmits the video data and audio data of the second user to the third terminal and transmits the video data and audio data of the third user to the second terminal, wherein when the current location of the third terminal approaches the current location of the second terminal, the video chat controller receives from the third terminal the video data of the third user, photographed by the camera of the third terminal, and the audio data including the voice of the third user, recorded by the microphone of the third terminal and transmit the video data and audio data of the third user to the second terminal, and the system further comprises a participant setting unit which transmits to a third terminal a signal asking an exercise participation intention received from a second terminal and receives a joint exercise start signal for accepting exercise participation from the third terminal, wherein when the third terminal transmits the joint exercise start signal to the second terminal through the participant setting unit, the image data controller displays on the third terminal the first exercise place image data corresponding to the current location of the second terminal.

Some implementations of the disclosed technology provide a system for providing a virtual exercise place, which is connected to terminals and fitness equipment capable of calculating an exercise distance and transmits an image of an exercise place to the terminals, the system comprising: an image information database which receives location-based image data related to the exercise place (hereinafter referred to as "exercise place image data"), generated by the first terminal, and stores the exercise place image data therein; and an image data controller transmitting the exercise place image data selected by a second terminal to the second terminal from the image information database, displaying on the second terminal the exercise place image data corresponding to the exercise start location received from the second terminal, receiving exercise distance information calculated by the fitness equipment connected to the second terminal, and displaying on the second terminal the exercise place image data corresponding to a location moved by an exercise distance from the exercise start location (hereinafter referred to as "current location").

In another aspect, the exercise place image data includes GPS coordinate values according to the movement path of the first terminal at the exercise place, and video data and audio data of the exercise place according to the GPS coordinate values.

In another aspect, the exercise place image data further comprises gradient data according to the GPS coordinate values at the exercise place, and the system further comprises a slope activation unit connected to a load control device of the fitness equipment connected to the second terminal and applying to the fitness equipment connected to the second terminal a load based on gradient data corresponding to the current location.

In another aspect, the second terminal and a third terminal include a camera and a microphone, wherein the system further comprises a video chatting controller receiving from the second terminal and the third terminal video data of a second user using the second terminal and a third user using the third terminal, photographed by the cameras of the second terminal and the third terminal, and audio data comprising voices of the second user and the third user, recorded by the microphones of the second terminal and the third terminal, transmitting the video data and audio data of the second user to the third terminal, and transmitting the video data and audio data of the third user to the second terminal, wherein when the current location of the third terminal is close to the current location of the second terminal, the video chatting controller receives from the third terminal the video data of the third user, photographed by the camera of the third terminal, and the audio data comprising the voice of the third user, recorded by the microphone of the third terminal, and transmitting the video data and audio data of the third user to the second terminal, wherein the system further comprises a participant setting unit transmitting to the third terminal a signal asking an exercise participation intention received from the second terminal and receiving a joint exercise start signal for accepting exercise participation from the third terminal, and wherein when the third terminal transmits the joint exercise start signal to the second terminal through the participant setting unit, the image data controller displays on the third terminal the exercise place image data corresponding to the current location of the second terminal.

In another aspect, the image data controller receives exercise distance information calculated by the fitness equipment connected to the second terminal and displays on the second terminal the exercise place image data corresponding to the current location of the fitness equipment connected to the second terminal.

In another aspect, the system further comprises a fitness equipment controller for controlling a speed of the fitness equipment connected to the second terminal, wherein the fitness equipment controller changes the speed of the fitness equipment connected to the second terminal according to the speed at which the current location of the exercise place image data changes.

BRIEF DESCRIPTION OF DRAWINGS

A brief description of each drawing is provided so that the drawings cited in this specification are understood more fully.

DETAILED DESCRIPTION

Figure 1:
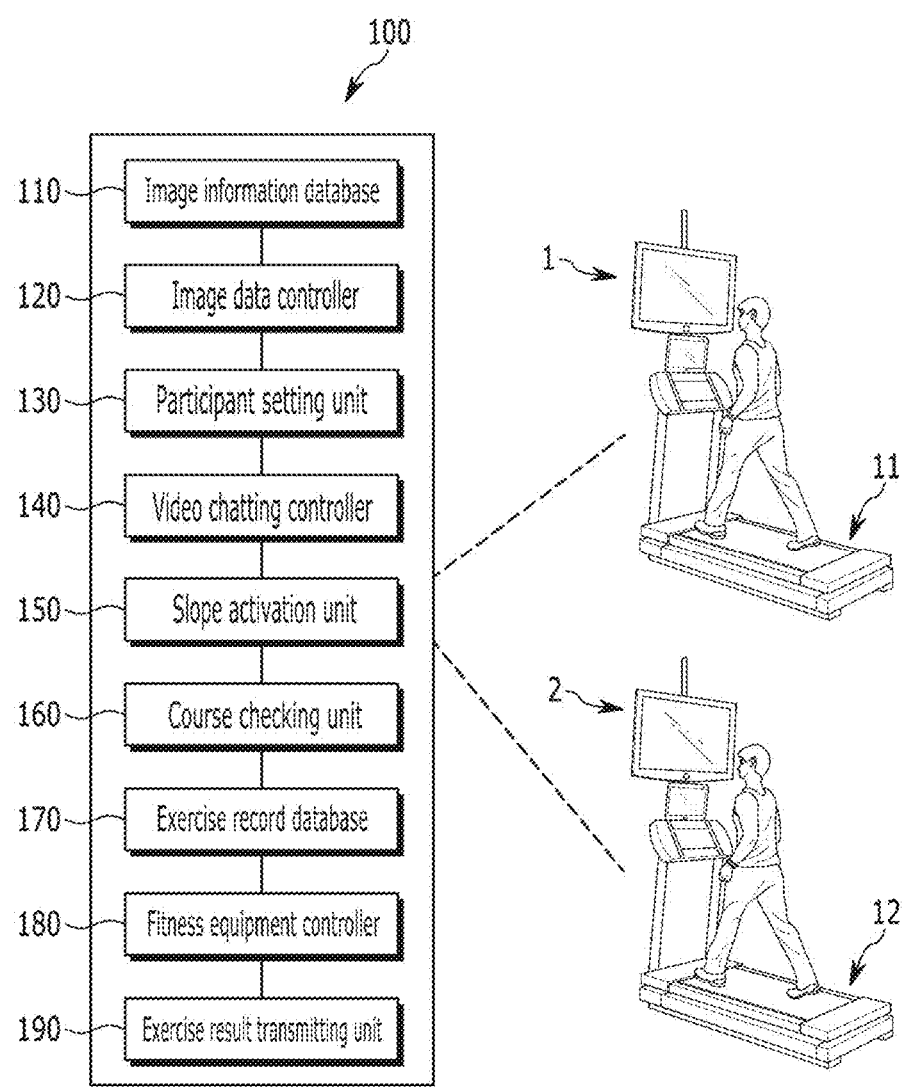
FIG. 1 is an exemplary diagram showing a schematic configuration of a system for providing a virtual exercise place according to an implementation of the disclosed technology.

Some implementations of the disclosed technology are illustrated in the drawings and are described in detail through the detailed description. It is however to be understood that the disclosed technology is not intended to be limited to the specific implementations and the disclosed technology includes all changes, equivalents and substitutions which fall within the spirit and technological scope of the disclosed technology.

Hereinafter, various implementations of the disclosed technology will be described in detail with reference to the accompanying drawings so that those skilled in the art can easily carry out the disclosed technology. In the following detailed description of the embodiments of the disclosed technology, a detailed description of known functions or configurations will be omitted. The same reference numerals are used throughout the drawings for portions having similar functions and actions. Furthermore, numbers (for example, the first and the second) used in the entire specification are merely identification symbols for distinguishing one element from the other element.

In addition, in the entire specification, when a part is referred to as being "connected" with another part, it is not only a case where it is directly connected, but also a case where it is indirectly connected with another element therebetween. Also, "comprising" and "including" mean that other components may be included, rather than excluding other components, unless specifically stated otherwise.

The term "unit" as used herein may include software, hardware, or a combination thereof depending on the context in which the term is used. For example, the software may be machine code, firmware, embedded code, application software, or a combination thereof. Also, for example, the hardware may be a circuit, a processor, a computer, an integrated circuit, integrated circuit cores, or a combination thereof. Two or more elements expressed as "unit" may be merged into a single element or one element may be divided into two or more elements for each subdivided function.

Hereinafter, various implementations of the disclosed technology will be described in detail with reference to the accompanying drawings so that those skilled in the art can easily carry out the disclosed technology.

Figure 2:
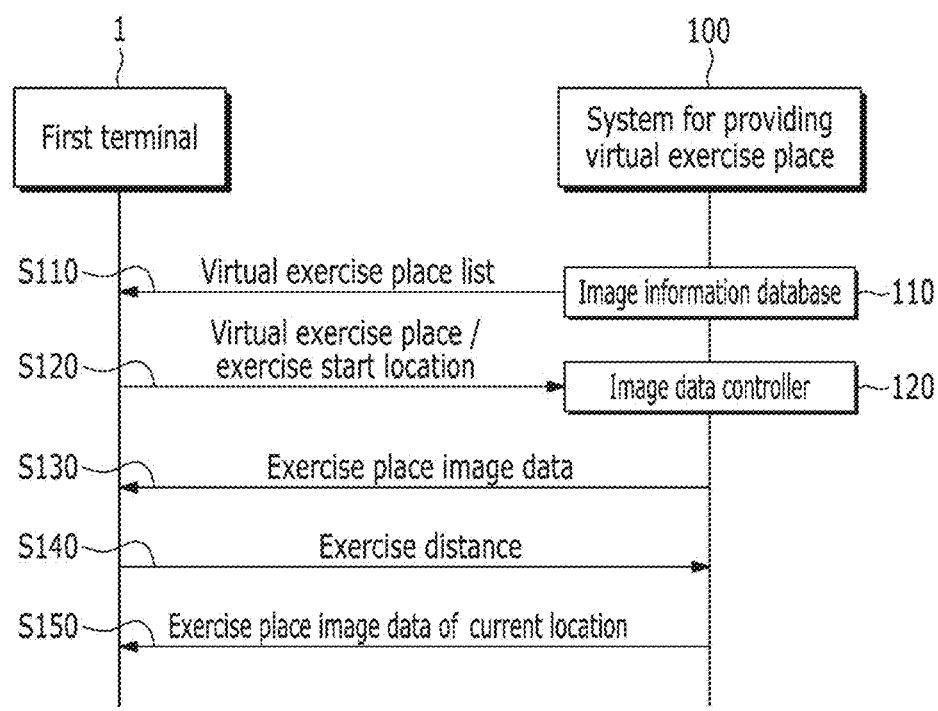
FIG. 2 is an exemplary flowchart showing a method of providing a virtual exercise place in the system for providing a virtual exercise place according to an implementation of the disclosed technology.

FIG. 1 is an exemplary diagram showing a schematic configuration of a system for providing a virtual exercise place according to an implementation of the disclosed technology. FIG. 2 is an exemplary flowchart showing a method of providing a virtual exercise place in the system for providing a virtual exercise place according to an implementation of the disclosed technology.

The system 100 for providing a virtual exercise place according to an embodiment of the disclosed technology may be connected to at least one terminal 1 and 2, and at least one piece of fitness equipment 11 and 12 capable of calculating an exercise distance over a network and perform a function of transmitting an image of a virtual exercise place to the terminal.

In this case, the network means connection architecture through which information can be exchanged between nodes, such as terminals, fitness equipment and servers. Examples of the network include a 3$^{rd}$ Generation Partnership Project (3GPP) network, a Long Term Evolution (LTE) network, a World Interoperability for Microwave Access (WIMAX) network, the Internet, a Local Area Network (LAN), a Wireless Local Area Network (Wireless LAN), a Wide Area Network (WAN), a Personal Area Network (PAN), a Bluetooth network, a satellite broadcasting network, an analog broadcasting network, and a Digital Multimedia Broadcasting (DMB) network, but are not limited thereto.

The terminal of a user may be implemented using a computer capable of accessing a server or terminal at a remote place over the network. In this case, the computer may include a notebook, desktop, laptop, etc. on which a web browser has been mounted, for example. Furthermore, the terminal of a user may be implemented using a terminal capable of accessing a server or terminal at a remote place over the network. The terminal of a user is a wireless communication device that guarantees portability and mobility, for example. The terminal may include all of kinds of handheld-based wireless communication devices, such as a Personal Communication System (PCS), a Global System for Mobile communications (GSM), Personal Digital Cellular (PDC), a Personal Handyphone System (PHS), a Personal Digital Assistant (PDA), International Mobile Telecommunication (IMT)-2000, Code Division Multiple Access (CDMA)-2000, W-Code Division Multiple Access (W-CDMA) and Wireless Broadband Internet (Wibro) terminals, a smartphone, a smartpad, and a tablet PC. The terminals 1 and 2 are installed on the front, side or upper part of the fitness equipment 11 and 12 and preferably include large-sized monitors capable of displaying an image. The terminals 1 and 2 may be connected to a large monitor installed in the fitness equipment 11 and 12 to transmit video and audio signals. Furthermore, the terminal preferably includes a camera and a microphone. The fitness equipment is fitness equipment, such as a treadmill or cycling equipment. Equipment using a method of calculating a moving distance based on exercise may be applied to the fitness equipment.

The system 100 for providing a virtual exercise place may include an image information database 110, an image data controller 120, a participant setting unit 130, a video chatting controller 140 and a slope activation unit 150.

The image information database 110 is a data storage server and may store location-based image data related to a virtual exercise place. For example, the image information database may store image data captured by a 360-degree camera every coordinate value based on GPS coordinates. Any place in the world may become a virtual exercise place. Furthermore, the image information database 110 may include gradient data corresponding to each location of location-based image data related to a virtual exercise place. For example, the image information database may store gradient data including a measured slope for all the directions of 360 degrees based on GPS coordinates.

Figure 3:
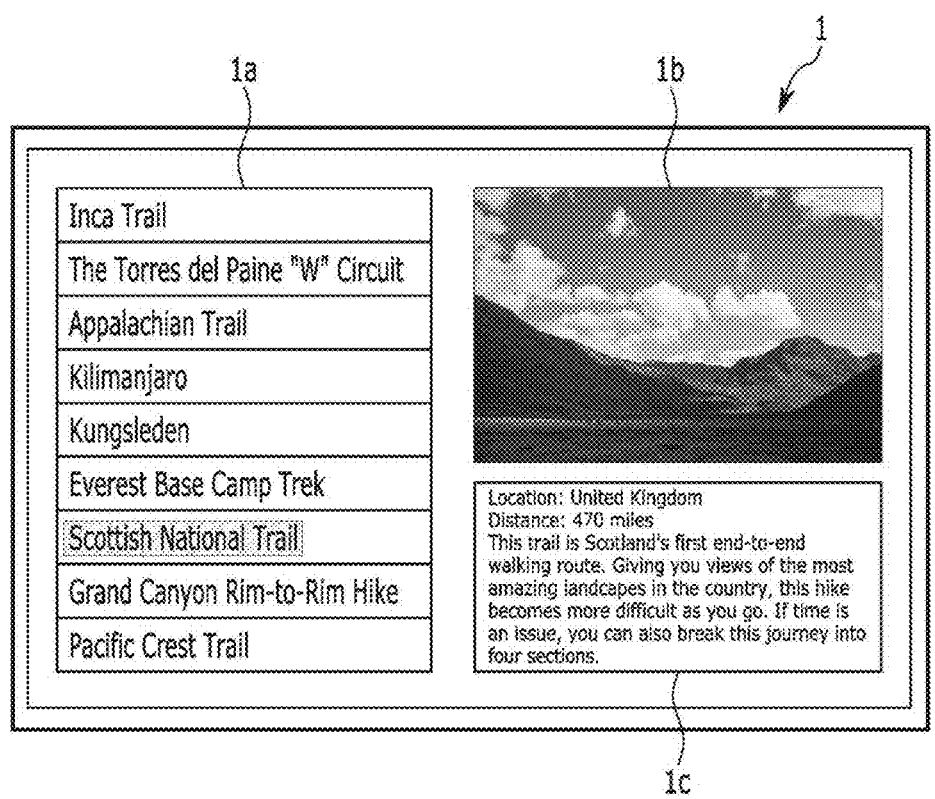
FIG. 3 is an exemplary diagram showing a virtual exercise place selection screen displayed in a terminal of the system for providing a virtual exercise place according to an implementation of the disclosed technology.
Figure 4:
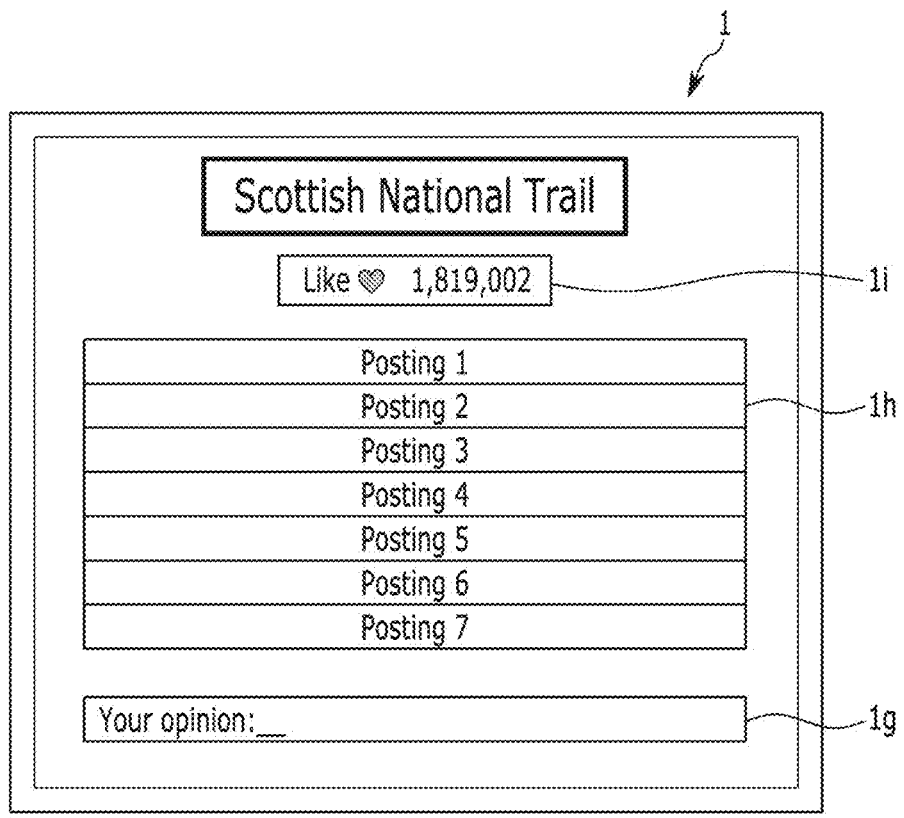
FIG. 4 is an exemplary diagram showing a posting screen for a virtual exercise place displayed on a terminal of the system for providing a virtual exercise place according to an implementation of the disclosed technology.
Figure 5:
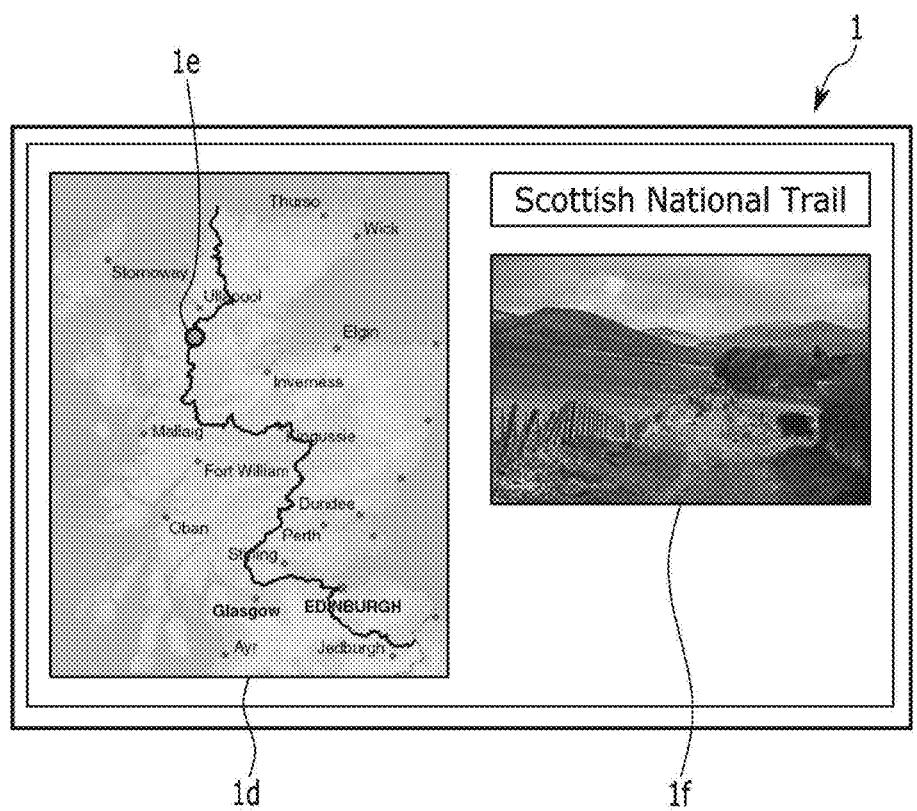
FIG. 5 is an exemplary diagram showing an exercise start location selection screen displayed on a terminal of the system for providing a virtual exercise place according to an implementation of the disclosed technology.

FIG. 3 is an exemplary diagram showing a virtual exercise place selection screen displayed in a terminal of the system for providing a virtual exercise place according to an implementation of the disclosed technology. FIG. 4 is an exemplary diagram showing a posting screen for a virtual exercise place displayed on a terminal of the system for providing a virtual exercise place according to an implementation of the disclosed technology. FIG. 5 is an exemplary diagram showing an exercise start location selection screen displayed on a terminal of the system for providing a virtual exercise place according to an implementation of the disclosed technology. The disclosed technology is not limited to the illustrated configuration.

A first user may access the image information database 110 through his or her own first terminal 1, may check a virtual exercise place list 1a (S110), and may select a virtual exercise place where the first user wants to take exercise. In order to help the selection of the first user, the first terminal 1 may receive a photo 1b and information 1c for the virtual exercise place written in the virtual exercise place list 1a from the image information database 110 and may display the received photo and information.

The virtual exercise place may include all of worldwide roads on which exercise can be taken. For example, in Korea, the virtual exercise place may include Cheonggye creek Night Walk, Way to Mount Seorak Towangseong Falls, DMZ Punch Bowl Dulle-gil Trail (Meonmejjaegil), Namhansanseong Dulle-gil Trail 5 Course (Seonggwak-gil), and so on.

The information 1c about the virtual exercise place may include information (history, length, difficulty, etc.) about the corresponding exercise place. In the information 1c about the virtual exercise place, an input window 1g in which a user's opinion about the virtual exercise place can be posted may be set to be displayed, and a list window 1h showing postings containing the user's opinions may be displayed. In addition, the user may display his/her preference for the virtual exercise place by pressing the "Like" button through the preference input window 1i and check the number of "likes" pressed by other users. In this way, the first user can post his/her opinion on the virtual exercise place or read comments posted by other users. Such posting may be shared through other SNS programs (for example, Facebook, Instagram, KakaoStory and Pod cast). Contents and posting described in the information 1c about the virtual exercise place may be shared together.

When the first user selects the virtual exercise place, a screen 1d on which an exercise start location can be selected is displayed in the first terminal 1. Courses capable of exercise in the virtual exercise place are displayed, and the user may select an exercise start location 1e. When the user selects the exercise start location 1e, a scene 1f seen at the front from the exercise start location 1e is displayed. The scene 1f may be changed depending on the exercise direction.

The image data controller 120 receives from the first terminal 1 the virtual exercise place and the exercise start location (S120), and may select location-based image data related to the virtual exercise place (hereinafter referred to as "exercise place image data") in the image information database 110 and transmit the exercise place image data to the first terminal 1 (S130). For example, the image data controller 120 may select exercise place image data corresponding to the GPS coordinates of the virtual exercise place selected by the first user, and may transmit the selected exercise place image data to the first terminal 1. The image 1f of the exercise place image data may be displayed in the first terminal. In FIG. 5, the image if of the exercise place image data has been illustrated as a small screen, but may be changed into a mode in which the exercise place image data is displayed on a full screen.

The image data controller 120 may receive exercise distance information calculated by the first fitness equipment 11 from the first terminal 1 connected to the first fitness equipment 11 (S140), and may display in the first terminal 1 the image of the exercise place image data corresponding to the location moved by an exercise distance from the exercise start location (hereinafter referred to as a "current location") (S150). For example, the image data controller 120 may obtain exercise distance information through a known distance calculator mounted on a treadmill or cycling equipment and the first terminal 1 connected thereto using a wired/wireless method. The image data controller 120 may select from the image information database 110 the exercise place image data corresponding to the GPS coordinates of the virtual current location into which exercise distance information has been incorporated, and may transmit the selected exercise place image data to the first terminal 1. The image 1f of the exercise place image data for the virtual current location may be displayed in the first terminal 1.

As described above, when the first user takes exercise in the first fitness equipment, the exercise place image data continues to be updated in real time. As if the first user enters the virtual exercise place and takes exercise, a scene displayed to the first user in the first terminal 1 is changed in accordance with an exercise distance.

The slope activation unit 150 may apply a load, corresponding to gradient data corresponding to a virtual current location, to the first fitness equipment 11 or may apply a gradient, corresponding to gradient data corresponding to a virtual current location, to the first fitness equipment 11 through the first terminal 1 connected to the load control device of the first fitness equipment 11 in a wired/wireless way. For example, when a slope increases, the slope activation unit may increase a load of cycling equipment or increase the foothold slope of a treadmill, thereby making exercise of the first user more difficult.

Figure 6:
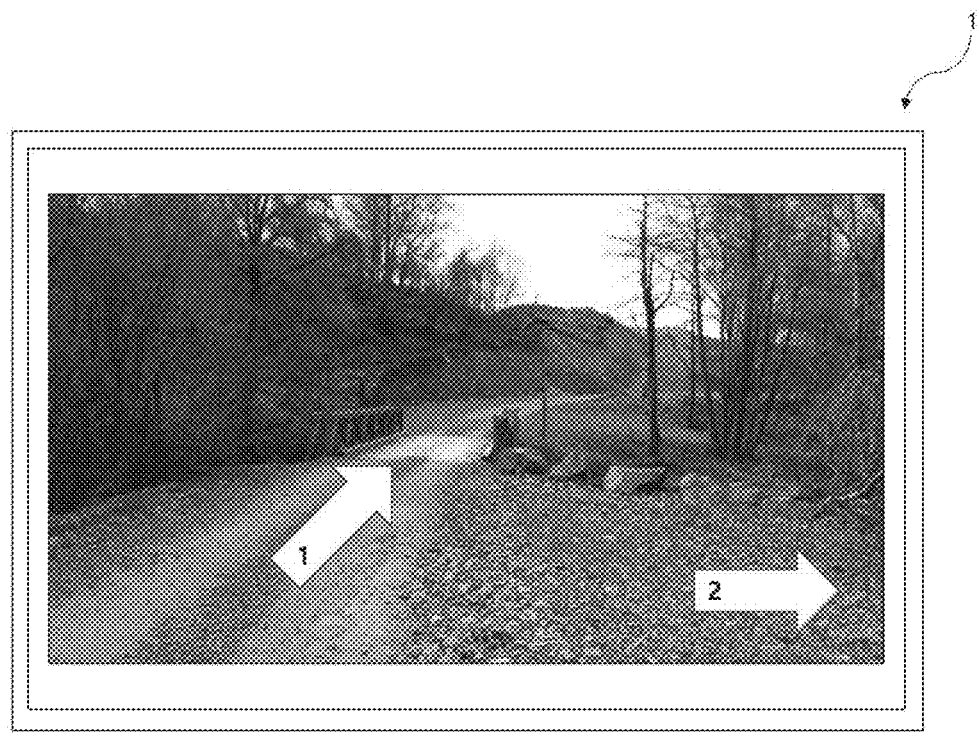
FIG. 6 is an exemplary diagram showing a course change screen displayed in a terminal of the system for providing a virtual exercise place according to an implementation of the disclosed technology.

FIG. 6 is an exemplary diagram showing a course change screen displayed in a terminal of the system for providing a virtual exercise place according to an implementation of the disclosed technology.

The system for providing a virtual exercise place according to an implementation of the disclosed technology may further comprise course checking unit 160.

While the first user takes exercise according to a course first determined in the first fitness equipment, the first user may change the course into a new course. The image data controller 120 may transmit a course selection message, including information indicating that the course may be changed and courses that may be selected, to the first terminal 1 when the virtual current location reaches a course selection point (for example, a forked road) of the exercise place image data. The first user may select a desired course (for example, No. 1 arrow or No. 2 arrow in FIG. 6) through the first terminal 1. The image data controller 120 may display in the first terminal 1 the image of the exercise place image data corresponding to the course selected by the first terminal 1.

The camera installed in the first terminal 1 may photograph the movement of the user's hand during exercise, and the course checking unit 160 may search for the previously stored movement pattern matching the movement of the user's hand and then matches the pattern. The course checking unit 160 may determine the path intended by the user according to the command given to the matching movement pattern. For example, when the user swipes the hand from left to right, the course checking unit 160 finds a pattern of swinging the hand from left to right among the stored movement patterns, and If the meaning of the pattern is set to select the right road, the course checking unit 160 may determine that the right road is selected at the course selection point, and the image data controller 120 may display the selected right road.

Figure 7:
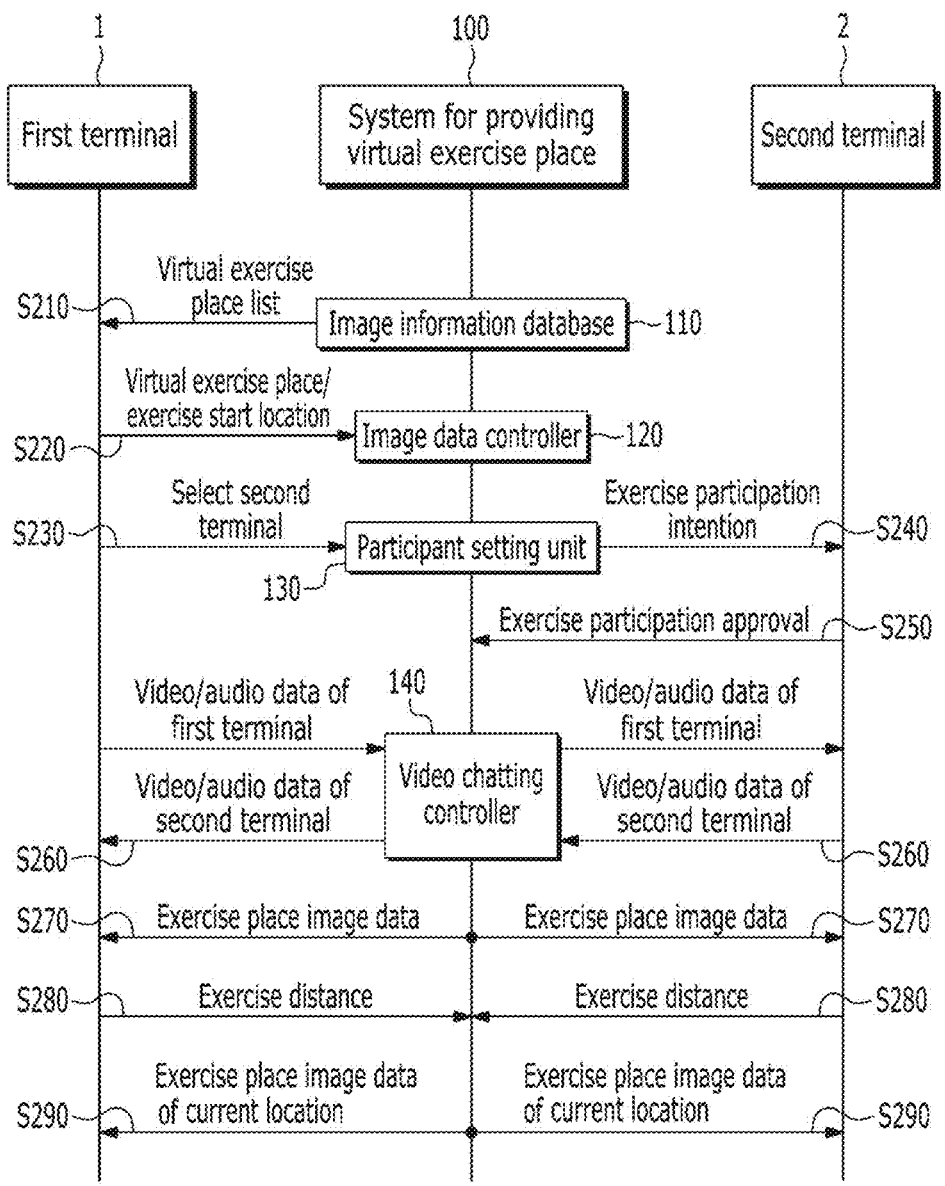
FIG. 7 is an exemplary flowchart showing a method of providing a virtual exercise place applied when a plurality of users uses the system for providing a virtual exercise place according to an implementation of the disclosed technology.
Figure 8:
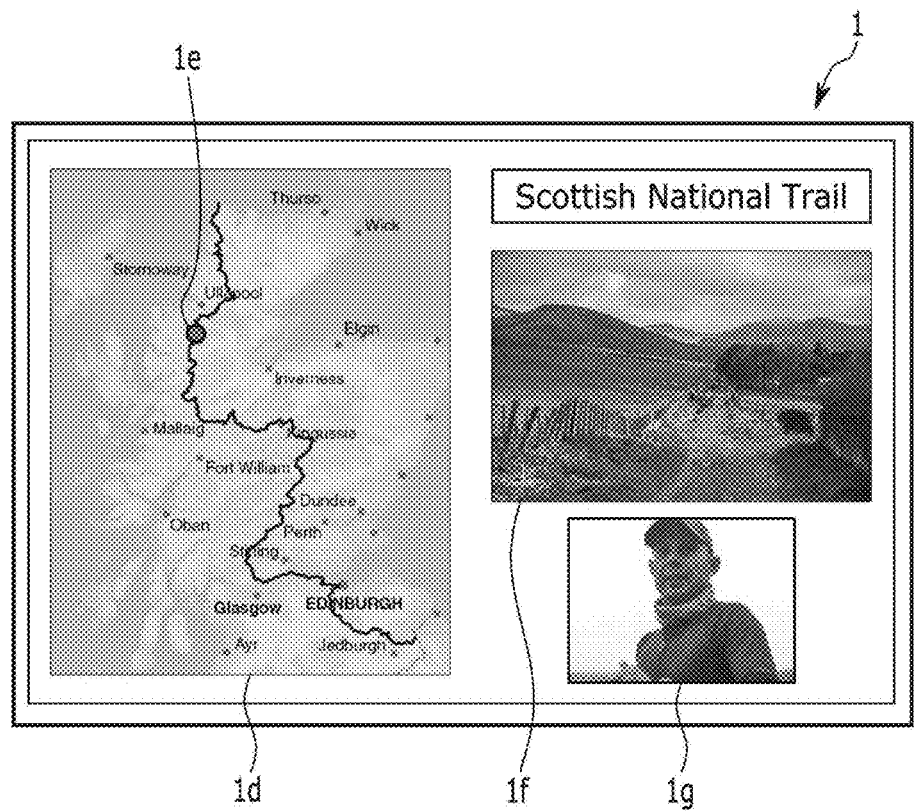
FIG. 8 is an exemplary diagram showing an exercise start location selection screen displayed in a terminal if a plurality of users uses the system for providing a virtual exercise place according to an implementation of the disclosed technology.

FIG. 7 is an exemplary flowchart showing a method of providing a virtual exercise place applied when a plurality of users uses the system for providing a virtual exercise place according to an implementation of the disclosed technology. FIG. 8 is an exemplary diagram showing an exercise start location selection screen displayed in a terminal if a plurality of users uses the system for providing a virtual exercise place according to an implementation of the disclosed technology.

A first user may access the image information database 110 through his or her own first terminal 1, may check the virtual exercise place list 1*a* (S210), and may select a virtual exercise place where the first user wants to take exercise. As shown in FIG. 3, in order to help the selection of the first user, the first terminal 1 may receive the photo 1*b* and information 1*c* for the virtual exercise place written in the virtual exercise place list 1*a* from the image information database 110, and may display the received photo 1*b* and information 1*c*.

The virtual exercise place may include all of worldwide roads on which exercise can be taken. For example, in Korea, the virtual exercise place may include Cheonggye creek Night Walk, Way to Mount Seorak Towangseong Falls, DMZ Punch Bowl Dulle-gil Trail (Meonmejjaegil), Namhansanseong Dulle-gil Trail 5 Course (Seonggwak-gil), and so on.

The information 1*c* about the virtual exercise place may include information (history, length, difficulty, etc.) about the corresponding exercise place. In the information 1*c* about the virtual exercise place, an input window 1*g* in which a user's opinion about the virtual exercise place can be posted may be set to be displayed, and a list window 1*h* showing postings containing the user's opinions may be displayed. In addition, the user may display his/her preference for the virtual exercise place by pressing the "Like" button through the preference input window 1*i* and check the number of "likes" pressed by other users. In this way, the first user can post his/her opinion on the virtual exercise place or read comments posted by other users. Such posting may be shared through other SNS programs (for example, Facebook, Instagram, KakaoStory and Pod cast). Contents and posting described in the information 1*c* about the virtual exercise place may be shared together.

When the first user selects the virtual exercise place, the screen 1*d* on which an exercise start location can be selected is displayed in the first terminal 1 as shown in FIG. 5. Courses on which exercise can be taken in the virtual exercise place are displayed. The user may select the exercise start location 1*e* (S220). When the user selects the exercise start location 1*e*, the front scene 1*f* seen from the exercise start location 1*e* is displayed.

The first user may select one or more partners with whom the first user can take exercise in the virtual exercise place. The first user may select a second user as a partner with whom the first user will take exercise through the first terminal 1. The first terminal 1 transmits a signal, providing notification that the second user has been selected as a partner with whom the first user will take exercise, to the participant setting unit 130 (S230). The second user may be a person who lives in a different country and may be a person who takes exercise in the same place. The participant setting unit 130 may transmit to the first terminal 1 a list of users who have accessed the system for providing a virtual exercise place so that the first user can easily select a partner with whom the first user will take exercise.

A signal asking an exercise participation intention may be transmitted from the participant setting unit 130 to the second terminal 2 of the second user (S240). The second user may transmit a joint exercise start signal for accepting exercise participation to the participant setting unit 130 (S250) or may transmit a joint exercise refusal signal for rejecting exercise participation to the participant setting unit 130 through the second terminal 2. When the participant setting unit 130 receives the joint exercise start signal from the second terminal 2, an image 1*g* of the second user photographed by the second terminal 2 is displayed in the first terminal 1.

In FIGS. 1 and 7, the system 100 for providing a virtual exercise place has been illustrated as being connected to the two terminals 1 and 2, but this is only an example for convenience of description of the disclosed technology. Three or more terminals may be connected to the system 100 for providing a virtual exercise place. Accordingly, the system 100 for providing a virtual exercise place may be used in group exercise of a group, such as a club, and may use a method in which celebrities who have approved exercise participation from among the celebrities of internal and external sports, medicine, entertainment, politics, culture and art fields participate in exercise along with multiple users. Furthermore, the participant setting unit 130 may include a virtual character (famous comic character, character having an image of himself or herself or celebrity, a virtual trainer character, etc.) in a list of partners with whom the first user will take exercise, and may provide the list to the first terminal 1. Such methods can greatly enhance users' interest and a degree of participation. The video chatting controller 140 may receive from the first terminal 1 video data, including an image of the first user photographed by the camera of the first terminal 1, and audio data, including the voice of the first user recorded by the microphone of the first terminal 1, and may receive from the second terminal 2 video data, including an image of the second user photographed by the camera of the second terminal 2, and audio data, including the voice of the second user recorded by the microphone of the second terminal 2. The video chatting controller 140 may transmit the video data and audio data of the first user to the second terminal 2, and may transmit the video data and audio data of the second user to the first terminal 1 (S260).

If a virtual character has been selected as a partner with whom the first user will take exercise, the video chatting controller 140 may transmit the video data and audio data of the selected character to the first terminal 1. In this case, the virtual character may talk and behave according to artificial intelligence. Preferably, the virtual character runs at the same speed as the first user.

Furthermore, the video chatting controller 140 may transmit background music (song, pop song, classical music, etc.) to the terminals 1 and 2 so that the users can take exercise along with the background music.

After the virtual exercise place and the exercise start location are received from the first terminal 1, the image data controller 120 may select exercise place image data from the image information database 110 and transmit it to the first terminal 1 and the second terminal 2 (S270). For example, the image data controller 120 may select exercise place image data corresponding to the GPS coordinates of the virtual exercise place selected by the first user, and may transmit the selected exercise place image data to the first terminal 1 and the second terminal 2. The image 1*f* of the exercise place image data may be displayed in the first terminal 1 and the second terminal 2. In FIG. 8, each of the image 1*f* of the exercise place image data and the image 1*g* of the second user has been illustrated as a small screen, but may be changed into a mode in which the image of the exercise place image data and the image of the second user are displayed on a full screen.

The image data controller 120 may receive exercise distance information calculated by the first fitness equipment 11 (S280), and may display the image of the exercise place image data corresponding to a virtual current location to the first terminal 1 and the second terminal 2 (S290). For example, the image data controller 120 may obtain the exercise distance information through a known distance calculator mounted on a treadmill or cycling equipment and the first terminal 1 and the second terminal 2 connected thereto using a wired/wireless method. The image data controller 120 may select from the image information database 110 exercise place image data corresponding to the GPS coordinates of a virtual current location into which the exercise distance information has been incorporated, and may transmit the selected exercise place image data to the first terminal 1 and the second terminal 2. The image 1*f* of the exercise place image data for the virtual current location may be displayed in the first terminal 1 and the second terminal 2.

In this way, as the first user and the second user take exercise in the first fitness equipment and the second fitness equipment, respectively, the image of the exercise place image data continues to change. As if the first user and the second user enter the virtual exercise place and take exercise together, scenes displayed to the first user and the second user through the first terminal 1 and the second terminal 2 are changed in accordance with an exercise distance.

There may be a difference between the virtual current location of the first user and the virtual current location of the second user due to a difference in the exercise speed between the first user and the second user. In this case, different exercise place image data may be displayed in the first terminal 1 and the second terminal 2.

The slope activation unit 150 may apply to the first fitness equipment 11 and the second fitness equipment 12 a load, corresponding to gradient data corresponding to a virtual current location, or apply a gradient, corresponding to the gradient data corresponding to the virtual current location, to the first fitness equipment 11 and the second fitness equipment 12 through the first terminal 1 and second terminal 2 connected to the load control devices of the first fitness equipment 11 and the second fitness equipment 12 in a wired/wireless manner. For example, when the slope increases, the slope activation unit 150 may increase a load (rolling resistance) of cycling equipment or increase the foothold slope of a treadmill, thereby being capable of making further difficult exercise of the first user and the second user.

Meanwhile, while the first user and the second user take exercise on a course first determined in the first terminal 1, they may change the course into a new course. When a virtual current location reaches a course selection point (for example, a forked road) of exercise place image data, the image data controller 120 may transmit to the first terminal 1 and/or the second terminal 2 a course selection message, including information indicating that the course may be changed and courses that may be selected. Any one of the first user and the second user may select a desired course (for example, No. 1 arrow or No. 2 arrow of FIG. 6) through the first terminal 1 or the second terminal 2. Exercise place image data corresponding to a course first selected by any one of the first terminal 1 and the second terminal 2 may be displayed in the first terminal 1 and the second terminal 2. Accordingly, a user who has first reached a forked road has priority to determine a course, and thus there is an effect in that an interest in exercise can be increased through a competition.

Furthermore, when the virtual current location of another user who accesses the system 100 and takes exercise is close to the virtual current location of the first user or the second user, the video chatting controller 140 may display an image of another user in the first terminal 1 and the second terminal 2 and output a voice of another user through the first terminal 1 and the second terminal 2, whereby the video chatting controller 140 can notify the first user and the second user that another user takes exercise in the place where the first user and the second user take exercise. Accordingly, exchange between users can become active, and users can have an interest in virtual moving exercise so that they are further immersed in the virtual exercise space. Users who have met together in the virtual exercise place as described above may move together by transmitting a joint signal through the participant setting unit 130. In this case, the same exercise place image data may be displayed in the terminals of the users.

In detail, when the virtual current location of the third terminal, which the first terminal 1 has not asked to participate in the exercise, approaches the virtual current location of the first terminal 1 or the second terminal 2, the video chatting controller 140 may receive from the third terminal the video data of the third user using the third terminal, photographed by the camera of the third terminal and audio data including a voice of the third user, recorded by a microphone of the third terminal, transmit the video data and audio data of the third user to the first terminal and the second terminal, and transmit the video data and audio data of the first user and second user to the third terminal. Furthermore, the participant setting unit 130 may transmit the information (e.g., name, photo, gender, etc.) of the third user to the first terminal 1 and the second terminal 2, and conversely, transmit the information (e.g., name, photo, gender, etc.) of the first user and second user to the third terminal.

The first user or the second user can select the third user as a companion to exercise together via the first terminal 1 or the second terminal 2, and for this purpose the first terminal 1 or the second terminal 2 may transmit a signal indicating that the third user is selected as the exercise companion to the participant setting unit 130.

The participant setting unit 130 may transmit to the third terminal of the third user a signal for asking for an exercise participation intention, and the third user may transmit to the participant setting unit 130 a joint exercise start signal for accepting exercise participation through the third terminal, or transmit to the participant setting unit 130 a joint exercise refusal signal for rejecting exercise participation. When the participant setting unit 130 receives the joint exercise start signal from the third terminal, the first terminal 1 and the second terminal 2 may display the third user photographed by the third terminal.

The third user can select the first user and the second user as a companion to exercise together via the third terminal, and for this purpose the third terminal may transmit a signal indicating that the first user and second user are selected as the exercise companion to the participant setting unit 130.

The signal for inquiring to participate in the exercise may be transmitted to the first terminal 1 of the first user and the second terminal 2 of the second user by the participant setting unit 130. The first user or the second user may transmit the joint exercise start signal to the participant setting unit 130 to accept the exercise participation through the first terminal 1 or the second terminal 2, or transmit the joint exercise refusal signal to the participant setting unit 130 to reject the exercise participation. When the participant setting unit 130 receives the joint exercise start signal from the first terminal 1 or the second terminal 2, the third terminal may display the first user and the second user, photographed by the first terminal and the second terminal.

As such, when the first user, the second user, and the third user exercise together, the same exercise place image data may be displayed on the first terminal 1, the second terminal 2, and the third terminal 3.

The system 100 for providing a virtual exercise place may provide an event to users who take exercise together.

The image data controller 120 may provide a first-come-first-served event of a predetermined section (which may be a path away from the initial path) to the users who exercise together, and the users may autonomously select a course at each forked road and run at full speed to first reach a target point. When the event starts, independent exercise place image data is displayed in the terminals of the users. The participant setting unit 130 may provide a reward, such as that the period of use of the system 100 is extended, to a user who has first reached the target point. When all the users reach the target point, the image data controller 120 may transmit the same exercise place image data to the terminals of the users like in the beginning, so the users can take exercise together.

Figure 9:
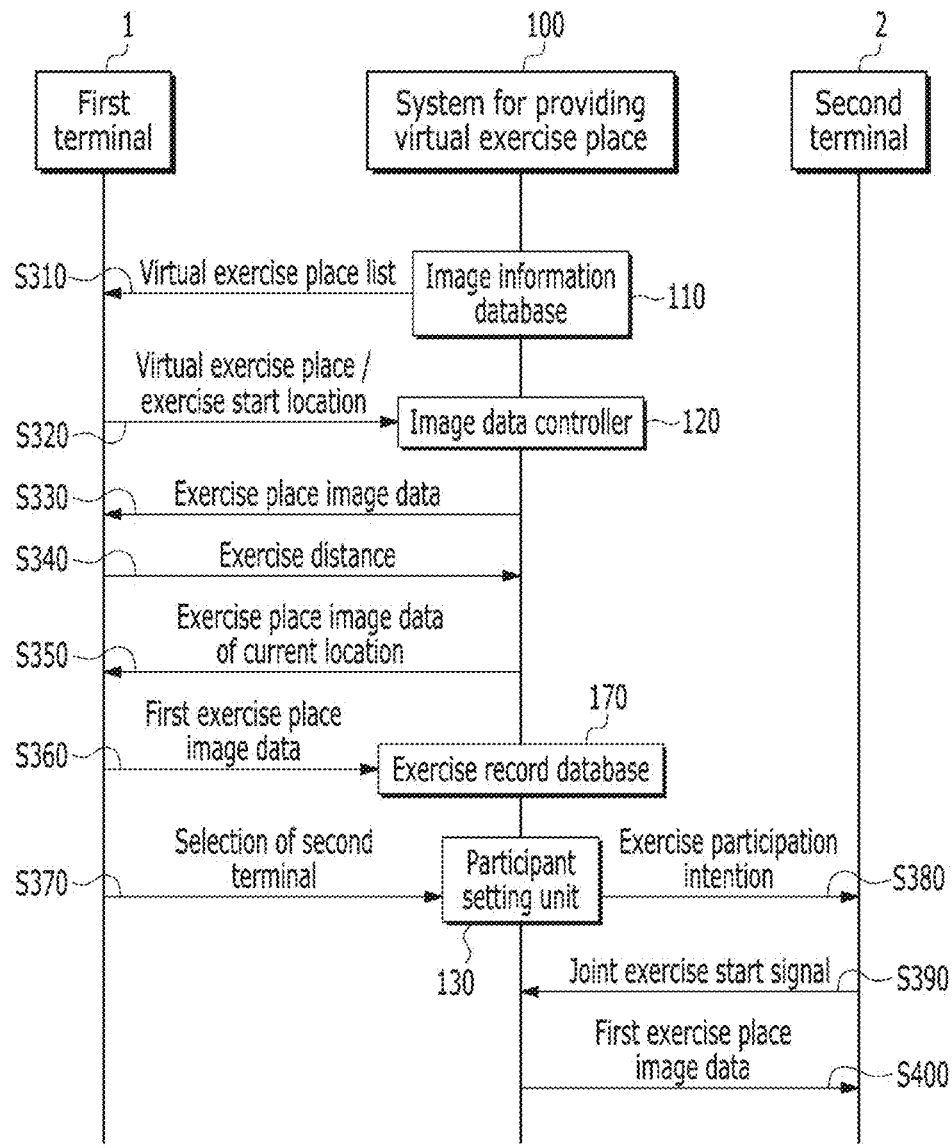
FIG. 9 is an exemplary flowchart showing a virtual exercise place providing method applied to a case where a plurality of users use the system for providing a virtual exercise place according to an implementation of the disclosed technology at a time difference.

FIG. 9 is an exemplary flowchart showing a virtual exercise place providing method applied to a case where a plurality of users use the system for providing a virtual exercise place according to an implementation of the disclosed technology at a time difference.

The system for providing a virtual exercise place according to an implementation of the disclosed technology may further comprise an exercise record database 170, a fitness equipment controller 180 and an exercise result transmitting unit 190.

The exercise record database 170 may be used in a situation in which the first user and the second user cannot exercise at the same time. For example, the first user may live in Korea, and the second user may live in the United States, and thus they cannot exercise together due to time difference.

After the first user accesses the image information database 110 through his/her first terminal 1 and checks the virtual exercise place list 1*a* (S310), the first user may select a virtual exercise place that he/she wants to exercise. In order to assist the first user in selecting the virtual exercise place, the first terminal 1 may receive a picture 1*b* and information 1*c* of the virtual exercise place described in the virtual exercise place list 1*a* from the image information database 110 and display the picture 1*b* and information 1*c* thereon.

When the first user selects the virtual exercise place, the first terminal 1 may display a screen 1*d* for selecting an exercise start location. The first terminal 1 may display courses for exercising at the virtual exercise location, and the first user can select the exercise start location 1*e*. When the first user selects the exercise start location 1*e*, the landscape 1*f* shown from the exercise start location 1*e* may be displayed. The landscape 1*f* will change according to the direction of movement.

The image data controller 120 may receive the virtual exercise place and the exercise start location from the first terminal 1 (S320), select the exercise place image data from the image information database 110 and transmit it to the first terminal 1 (S330). For example, the image data controller 120 may select the exercise place image data corresponding to the GPS coordinates of the virtual exercise place selected by the first user and transmit it to the first terminal 1, and the first terminal 1 may display the exercise place image data thereon.

The image data controller 120 may receive the movement distance information calculated by a first fitness equipment 11 from the first terminal 1 connected to the first fitness equipment 11 (S340), and the exercise place image data corresponding to the current location may be displayed on the first terminal 1 (S350). For example, the image data controller 120 may obtain the movement distance information through the first terminal 1 connected by a wired/wireless method to a known distance calculator mounted on a tread mill or a cycle mechanism, and the exercise place image data corresponding to the GPS coordinates of the current location reflecting the exercise distance information may be selected from the image information database 110 and transmitted to the first terminal 1, and the exercise place image data 1*f* for the current location may be displayed on the first terminal 1.

As the first user exercises on the first fitness equipment, the exercise place image data may be continuously updated in real time, and as if the first user exercises at the virtual exercise place, the scenery seen through the first terminal 1 to the first user may change in correspondence with the exercise distance.

Exercise place image data from the exercise start location displayed on the first terminal 1 to the current location (hereinafter referred to as "first exercise place image data") may be stored in the exercise record database 170 (S360). The first exercise place image data may comprise video data of the first user who uses the first fitness equipment, photographed by a camera of the first terminal 1, and audio data that includes the voice of the first user, recorded by a microphone of the first terminal 1.

The first user may select one or more users to whom he/she wants to provide the first exercise place image data. The first user can select the second user as a user to whom he/she wants to provide the first exercise place image data through the first terminal 1, and the first terminal 1 may transmit to the participant setting unit 130 a signal indicating that the second user has been selected as a user to whom the first user wants to provide the first exercise place image data (S370). The participant setting unit 130 may transmit to the second terminal 2 of the second user a signal for asking the exercise participation intention (S380).

The second user who starts the exercise at a time different from the time when the first user has exercised may transmit to the participant setting unit 130 the joint exercise start signal for accepting the exercise participation through the second terminal 2 (S390), or transmit to the participant setting unit 130 the joint exercise refusal signal for rejecting the exercise participation. When the participant setting unit 130 receives the joint exercise start signal from the second terminal 2, the image data controller 120 may display the first exercise place image data stored in the exercise record database 170 (S400).

The image data controller 120 may receive the movement distance information calculated by the second fitness equipment, and display on the second terminal the first exercise place image data corresponding to the current location calculated by the second fitness equipment.

The fitness equipment controller 180 may control the speed of the second fitness equipment. The fitness equipment controller 180 may change the speed of the second fitness equipment in accordance with the speed at which the current location of the first exercise place image data changes. In other words, the movement speed of the second fitness equipment is set in accordance with the speed at which the first user exercised. Accordingly, the second user may exercise at the exercise intensity of the first user, and as the video data and the audio data of the first user are provided, the second user may have a certain feeling of exercising with the first user.

The exercise result transmitting unit 190 may display composite image data combining the video data of the second user using the second fitness equipment, photographed by the camera of the second terminal 2, and/or the audio data including the voice of the second user using the second fitness equipment, recorded by the microphone of the second terminal 2, with the first exercise place image data, and after the composite image data displayed on the second terminal is stored in the exercise record database 170, it may be transmitted to the member account of the first user.

When the current location of another user (third user) who connects to the system 100 approaches the current location of the second user, the video chat controller 140 may display the appearance of the third user on the second terminal 2 and output the voice of the third user, thereby indicating that other users are exercising at the place where the second user is exercising. In this way, the interaction between the users can be actively performed, and the fun of the virtual movement exercise can be given to the users so that they can be more immersed in the virtual exercise place.

Specifically, when the current location of the third terminal of the third user approaches the current location of the second terminal 2, the video chat controller 140 receives from the third terminal the video data of the third user using the third terminal, photographed by the camera of the third terminal, and the audio data including the voice of the third user, recorded by the microphone of the third terminal, transmit the video data and audio data of the third user to the second terminal, and transmit the video data and audio data of the second user to the third terminal. In addition, the participant setting unit 130 may transmit the information (e.g., name, photo, gender, etc.) of the third user to the second terminal 2, and conversely, transmit the information (e.g., name, photo, gender, etc.) of the second user to the third terminal.

The second user may select a third user as a companion to exercise together through the second terminal 2, and for this purpose, the second terminal 2 may transmit to the participant setting unit 130 a signal indicating that the third user is selected as an exercise companion.

The signal asking the intention to participate in the exercise may be transmitted to the third terminal of the third user by the participant setting unit 130. The third user may transmit a joint exercise start signal for accepting exercise participation to the participant setting unit 130 through the third terminal, or transmit a joint exercise refusal signal for rejecting exercise participation to the participant setting unit 130. When the participant setting unit 130 receives the joint exercise start signal from the third terminal, the second terminal 2 may display the appearance of the third user, photographed by the third terminal.

Meanwhile, the third user may select the second user as a companion to exercise together through the third terminal, and for this purpose, the third terminal may transmit to the participant setting unit 130 a signal indicating that the second user is selected as the exercise companion.

The signal asking the intention to participate in the exercise may be transmitted to the second terminal 2 of the second user by the participant setting unit 130. The second user may transmit to the participant setting unit 130 the joint exercise start signal for accepting the exercise participation through the second terminal 2, or transmit to the participant setting unit 130 the joint exercise refusal signal for rejecting the exercise participation. When the participant setting unit 130 receives the joint exercise start signal from the second terminal 2, the third terminal may display the appearance of the second user, photographed by the second terminal 2.

When the second user and the third user exercise together, the first exercise place image data may be displayed on the third terminal.

Figure 10:
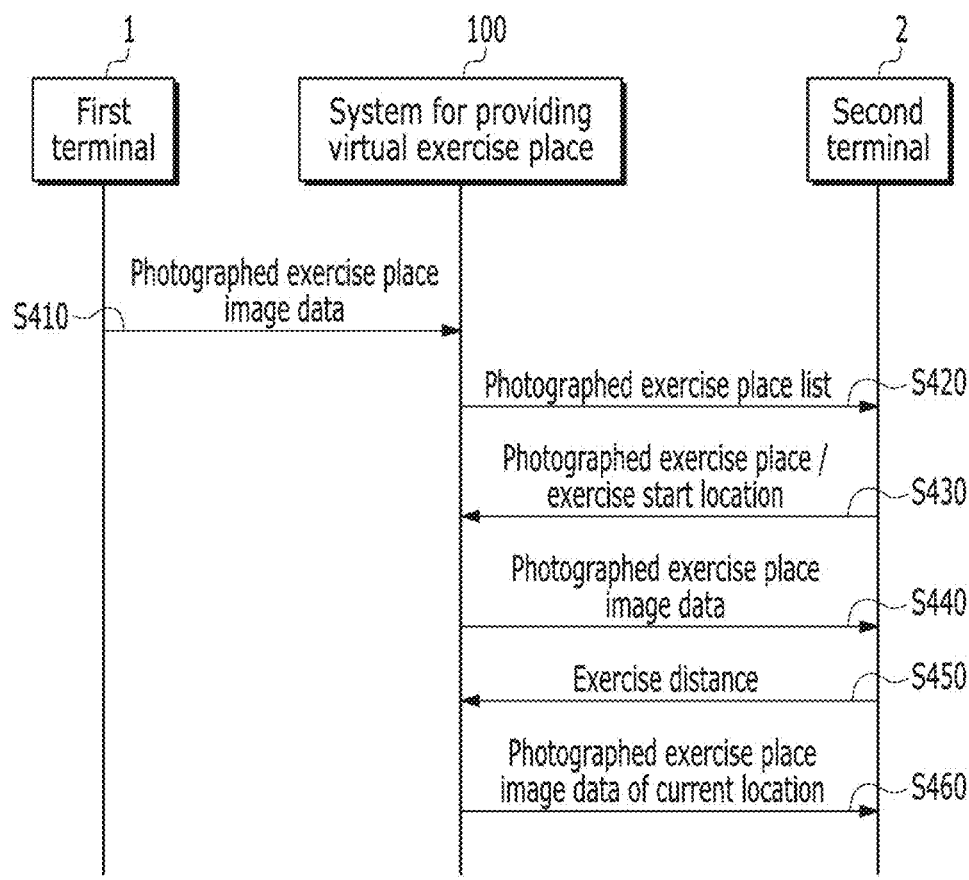
FIG. 10 is an exemplary flowchart showing a virtual exercise place providing method using exercise place image data generated by a user in the system for providing a virtual exercise place according to an implementation of the disclosed technology.

FIG. 10 is an exemplary flowchart showing a virtual exercise place providing method using exercise place image data generated by a user in the system for providing a virtual exercise place according to an implementation of the disclosed technology.

In the system for providing a virtual exercise place according to an implementation of the disclosed technology, The first user exercises at an actual exercise place, and the second user may exercise by using exercise place image data generated by the first terminal while the first user exercises (hereinafter referred to as "photographed exercise place image data").

The first user exercises at the actual exercise place. Here, the exercise is a movement of the way moving along the road, and for example may be running, walking, cycling, and the like. The exercise place may include all of worldwide roads on which exercise can be taken. For example, in Korea, the exercise place may include Cheonggye creek Night Walk, Way to Mount Seorak Towangseong Falls, DMZ Punch Bowl Dulle-gil Trail (Meonmejjaegil), Nam-hansanseong Dulle-gil Trail 5 Course (Seonggwak-gil), and so on.

At this time, the first terminal 1 may be attached to the body of the first user exercising in a state separated from the fitness equipment 11, generate the photographed exercise place image data and transmit the photographed exercise place image data to the image information database 110 (S410). In addition, the photographed exercise place image data may be stored in the image information database 110.

Here, the photographed exercise place image data may include the GPS coordinate value according to the movement route of the first terminal 1 at the actual exercise place, measured by the GPS sensor of the first terminal 1, video data of the actual exercise place photographed by the camera of the first terminal 1, and audio data of the actual exercise place, recorded by the microphone of the first terminal 1. In particular, the video data of the photographed exercise place image data is preferably generated by photographing the actual exercise place by the camera of the first terminal 1 so as to correspond to the gaze of the first user.

In addition, the photographed exercise place image data may include inclination data according to GPS coordinate values at the actual exercise place. For example, the inclination data may be generated by measuring the inclination of the moving direction of the first user based on the GPS coordinate value and stored in the terminal.

The photographed exercise place image data for the actual exercise place can be easily and arbitrarily generated by the first user using the first terminal 1, and in particular, as long as the exercise of the first user carrying the first terminal 1 is performed, the photographed exercise place image data can be created anywhere. The photographed exercise place image data may be transmitted to the image information database 110 and stored therein, and may be added to the photographed exercise place list. Here, the photographed exercise place list is composed of photographed exercise place image data, and the number of photographed exercise places can be easily increased by using the terminal.

On the other hand, when the photographed exercise place image data is transmitted from the first terminal 1 to the image information database 110, The first user may input information about the actual exercise place corresponding to the photographed exercise place image data into the image information database 110 through the first terminal 1. Therefore, the information about the actual exercise place corresponding to the photographed exercise place image data may be transmitted to the image information database 110 with the photographed exercise place image data.

The second user may access the image information database 110 through his/her second terminal 2, check the photographed exercise place list (see reference numeral "1a" in FIG. 3) (S420), and choose the photographed exercise place that he/she wants to exercise. In order to assist the selection of the second user, the second terminal 2 may receive from the image information database 110 a picture (see reference numeral "1b" in FIG. 3) and information (see reference numeral "1c" in FIG. 3) of the photographed exercise place described in the photographed exercise place list (see reference numeral "1a" in FIG. 3) and display them thereon.

When the second user selects the photographed exercise place generated by the first terminal 1, the second terminal 2 may display a screen for selecting an exercise start location (see reference numeral "1d" in FIG. 5). The paths where the second user can exercise at the photographed exercise location may be displayed, and the second user can select an exercise start location (see reference numeral "1e" in FIG. 5). When the second user selects the exercise start location, the landscape (see reference numeral "1f" in FIG. 5) taken by the first terminal 1 at the actual exercise place, shown at the exercise start location may be shown in the second terminal 2, and the landscape may change depending on the direction of movement.

The image data controller 120 may receive the photographed exercise place and the exercise start location from the second terminal 2 (S430), and selects the photographed exercise place image data from the image information database 110 and transmit it to the second terminal 2 (S440). For example, the image data controller 120 may select the photographed exercise place image data corresponding to the GPS coordinates of the photographed exercise place selected by the second user through the second terminal 2 and transmit the photographed exercise place image data to the second terminal 2, and the photographed exercise place image data may be displayed on the second terminal 2.

The image data controller 120 may receive the movement distance information calculated by the second fitness equipment 12 connected to the second terminal 2 from the second terminal 2 (S450), and display the photographed exercise place image data corresponding to the current location on the second terminal 2 (S460). For example, the image data controller 120 may obtain the movement distance information through the second terminal 2 connected in a wired or wireless manner with a known distance calculator mounted on a tread mill or a cycle mechanism. The image data controller 120 may select from the image information database 110 the photographed exercise place image data corresponding to the GPS coordinate value of the current location where the exercise distance information is reflected and transmit it to the second terminal 2. The second terminal 2 may display the photographed exercise place image data for the current location.

As the second user exercises using the second fitness equipment 12, the photographed exercise place image data is continuously updated in real time, and the scenery shown through the second terminal 2 to the second user (see reference numeral "1f" in FIG. 5) is changed according to the movement distance. That is, the second user can feel as if he/she is exercising by entering the actual exercise place where the first user exercised through the photographed exercise place image data.

The image data controller 120 may receive the movement distance information calculated by the second fitness equipment 12 and display the photographed exercise place image data corresponding to the current location of the photographed exercise place image data corresponding to the current location calculated by the second fitness equipment 12 on the second terminal 2.

The fitness equipment controller 180 may control the speed of the second fitness equipment 12. The fitness equipment controller 180 may change the speed of the second fitness equipment 12 in accordance with the speed at which the current location of the photographed exercise place image data changes. That is, the speed of the second fitness equipment 12 may be set in accordance with the speed at which the first user exercised at the actual exercise place. Accordingly, the second user can exercise at the exercise intensity that the first user exercised at the actual exercise place. In addition, as the video data and the audio data according to the exercise of the first user at the actual exercise place are provided through the second terminal 2, the second user has a feeling of exercising at the actual exercise place like the first user.

The slope activation unit 150 may apply a load, corresponding to gradient data corresponding to the current location, to the second fitness equipment 12 through the second terminal 2 connected to the load control device of the second fitness equipment 12 in a wired/wireless way, or may apply a gradient, corresponding to gradient data corresponding to the current location, to the second fitness equipment 12. For example, when a slope increases, the slope activation unit may increase a load of cycling equipment or increase the foothold slope of a treadmill, thereby making exercise of the second user more difficult.

When the current location of another user (third user) who connects to the system 100 approaches the current location of the second user, the video chat controller 140 may display the appearance of the third user on the second terminal 2 and output the voice of the third user, thereby indicating that other users are exercising at the place where the second user is exercising. In this way, the interaction between the users can be actively performed, and the fun of the virtual movement exercise can be given to the users so that they can be more immersed in the virtual exercise place.

Specifically, when the current location of the third terminal of the third user approaches the current location of the second terminal 2, the video chat controller 140 receives from the third terminal the video data of the third user using the third terminal, photographed by the camera of the third terminal, and the audio data including the voice of the third user, recorded by the microphone of the third terminal, transmit the video data and audio data of the third user to the second terminal, and transmit the video data and audio data of the second user to the third terminal. In addition, the participant setting unit 130 may transmit the information (e.g., name, photo, gender, etc.) of the third user to the second terminal 2, and conversely, transmit the information (e.g., name, photo, gender, etc.) of the second user to the third terminal.

The second user may select a third user as a companion to exercise together through the second terminal 2, and for this purpose, the second terminal 2 may transmit to the participant setting unit 130 a signal indicating that the third user is selected as an exercise companion.

The signal asking the intention to participate in the exercise may be transmitted to the third terminal of the third user by the participant setting unit 130. The third user may transmit a joint exercise start signal for accepting exercise participation to the participant setting unit 130 through the third terminal, or transmit a joint exercise refusal signal for rejecting exercise participation to the participant setting unit 130. When the participant setting unit 130 receives the joint exercise start signal from the third terminal, the second terminal 2 may display the appearance of the third user, photographed by the third terminal.

Meanwhile, the third user may select the second user as a companion to exercise together through the third terminal, and for this purpose, the third terminal may transmit to the participant setting unit 130 a signal indicating that the second user is selected as the exercise companion.

The signal asking the intention to participate in the exercise may be transmitted to the second terminal 2 of the second user by the participant setting unit 130. The second user may transmit to the participant setting unit 130 the joint exercise start signal for accepting the exercise participation through the second terminal 2, or transmit to the participant setting unit 130 the joint exercise refusal signal for rejecting the exercise participation. When the participant setting unit 130 receives the joint exercise start signal from the second terminal 2, the third terminal may display the appearance of the second user, photographed by the second terminal 2.

When the second user and the third user exercise together, the first exercise place image data may be displayed on the third terminal.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve described results. Moreover, the separation of various system components in the embodiments described in this patent document should not be understood as requiring such separation in all embodiments. Only a few implementations and examples are described. Other implementations, enhancements and variations can be made based on what is described and illustrated in this patent document.

DESCRIPTION OF REFERENCE NUMERALS

110: image information database
120: image data controller
130: participant setting unit
140: video chatting controller
150: slope activation unit
160: course checking unit
170: exercise record database
180: fitness equipment controller
190: exercise result transmitting unit

The invention claimed is:

1. A system for providing a virtual exercise place, which is connected to terminals and fitness equipment capable of calculating an exercise distance and transmits an image of an exercise place to the terminals, the system comprising:
   an image information database which receives location-based image data related to the exercise place (hereinafter referred to as "exercise place image data"), generated by the first terminal, and stores the exercise place image data therein; and
   an image data controller transmitting the exercise place image data selected by a second terminal to the second terminal from the image information database, displaying on the second terminal the exercise place image data corresponding to the exercise start location received from the second terminal, receiving exercise distance information calculated by the fitness equipment connected to the second terminal, and displaying on the second terminal the exercise place image data corresponding to a location moved by an exercise distance from the exercise start location (hereinafter referred to as "current location").

2. The system of claim 1, wherein the exercise place image data includes GPS coordinate values according to the movement path of the first terminal at the exercise place, and video data and audio data of the exercise place according to the GPS coordinate values.

3. The system of claim 1, wherein the exercise place image data further comprises gradient data according to the GPS coordinate values at the exercise place, and
   the system further comprises a slope activation unit connected to a load control device of the fitness equipment connected to the second terminal and applying to the fitness equipment connected to the second terminal a load based on gradient data corresponding to the current location.

4. The system of claim 1, wherein the second terminal and a third terminal include a camera and a microphone,
   wherein the system further comprises a video chatting controller receiving from the second terminal and the third terminal video data of a second user using the second terminal and a third user using the third terminal, photographed by the cameras of the second terminal and the third terminal, and audio data comprising voices of the second user and the third user, recorded by the microphones of the second terminal and the third terminal, transmitting the video data and audio data of the second user to the third terminal, and transmitting the video data and audio data of the third user to the second terminal,
   wherein when the current location of the third terminal is close to the current location of the second terminal, the video chatting controller receives from the third terminal the video data of the third user, photographed by the camera of the third terminal, and the audio data comprising the voice of the third user, recorded by the microphone of the third terminal, and transmitting the video data and audio data of the third user to the second terminal, wherein the system further comprises a participant setting unit transmitting to the third terminal a signal asking an exercise participation intention received from the second terminal and receiving a joint exercise start signal for accepting exercise participation from the third terminal, and wherein when the third terminal transmits the joint exercise start signal to the second terminal through the participant setting unit, the image data controller displays on the third terminal the exercise place image data corresponding to the current location of the second terminal.

5. The system of claim 1, wherein the image data controller receives exercise distance information calculated by the fitness equipment connected to the second terminal and displays on the second terminal the exercise place image data corresponding to the current location of the fitness equipment connected to the second terminal.

6. The system of claim 5, further comprising a fitness equipment controller for controlling a speed of the fitness equipment connected to the second terminal, wherein the fitness equipment controller changes the speed of the fitness equipment connected to the second terminal according to the speed at which the current location of the exercise place image data changes.

* * * * *